(12) United States Patent
Menéndez Martin et al.

(10) Patent No.: US 12,246,494 B2
(45) Date of Patent: Mar. 11, 2025

(54) METHOD FOR DETERMINING DEBONDING ENERGY OF A COMPOSITE LAMINATE

(71) Applicant: Airbus Operations S.L.U., Getafe (ES)

(72) Inventors: José Manuel Menéndez Martin, Getafe (ES); David López Bravo, Getafe (ES); Jagoba Alvaro Gordo, Getafe (ES); Raúl Martin Redondo, Getafe (ES)

(73) Assignee: AIRBUS OPERATIONS S.L.U., Getafe (ES)

( * ) Notice: Subject to any disclaimer, the term of this patent is extended or adjusted under 35 U.S.C. 154(b) by 172 days.

(21) Appl. No.: 17/584,841

(22) Filed: Jan. 26, 2022

(65) Prior Publication Data
US 2022/0242066 A1  Aug. 4, 2022

(51) Int. Cl.
*B29C 70/38* (2006.01)
*B29C 70/54* (2006.01)
*B29L 31/30* (2006.01)

(52) U.S. Cl.
CPC .......... *B29C 70/388* (2013.01); *B29C 70/384* (2013.01); *B29C 70/545* (2013.01); *B29L 2031/3076* (2013.01)

(58) Field of Classification Search
CPC ... B29C 70/388; B29C 70/386; B29C 70/384; B29C 70/382; B29C 70/38; B29C 70/545; B29L 2031/3076; B32B 43/006
See application file for complete search history.

(56) References Cited

U.S. PATENT DOCUMENTS 5,513,537 A * 5/1996 Brooks .................. G01N 19/04
73/865.8

FOREIGN PATENT DOCUMENTS

| CN | 113777024 A | * | 12/2021 | |
| EP | 3073262 A1 | * | 9/2016 | ........... B29C 70/382 |
| GB | 2533401 A | | 6/2016 | |
| JP | 2004177277 A | | 6/2004 | |

OTHER PUBLICATIONS

Translation EP-3073262-A1, Grohmann Y, Sep. 2016 (Year: 2016).*
European Search Report; priority document.

* cited by examiner

*Primary Examiner* — George R Koch
(74) *Attorney, Agent, or Firm* — Greer, Burns & Crain, Ltd.

(57) ABSTRACT

Automated manufacturing of composite laminates for structures, preferably structures of an aircraft, by using laying machines. More particularly, a method for determining the energy of debonding between layers of a laminate of composite material by means of a laying machine, and a laying machine for performing the method.

11 Claims, 2 Drawing Sheets

METHOD FOR DETERMINING DEBONDING ENERGY OF A COMPOSITE LAMINATE

CROSS-REFERENCES TO RELATED APPLICATIONS

This application claims the benefit of the European patent application No. 21382070.7 filed on Jan. 29, 2021, the entire disclosures of which are incorporated herein by way of reference.

FIELD OF THE INVENTION

The present invention relates to automated manufacturing of composite laminates for structures, preferably structures of an aircraft, by using laying machines. More particularly, the invention is related to a method for determining the energy of debonding between layers of a laminate of composite material by means of a laying machine. The present invention also relates to a laying machine for performing the method.

BACKGROUND OF THE INVENTION

The capability of a material to adhere itself, e.g., between its layers or to a solid surface, is known as tackiness or tack. This capability is a relevant property for a wide range of industrial applications and materials. Specifically, this capability of a material to adhere to itself or to another surface is a property extremely important for the manufacturing of fiber reinforced composite laminates, also called composite laminates. These composite laminates are manufactured by means of automated tape laying (ATL) machines or automated fiber placement (AFP) machines.

It is a key factor automating the operation of depositing a first layer over a laying tool, but it is also a critical factor that drives the productivity of the process of depositing the rest of the layers of a laminate and defines the final quality of the composite laminate part. Depositing the first layer of a composite laminate is always complex due to the specificities of the surfaces of the tools used for this operation over which this first layer is deposited. These laying tools are in most cases curing tools with very restrictive features linked to this function.

When preimpregnated reinforcements (prepreg) are used in the manufacturing of composite laminate, the tack or adherence of the material to itself or to the laying tool is mainly linked to the properties of the resin that impregnates the fibrous reinforcement and the level of impregnation of the reinforcement. This tack or adherence is also linked to the particularities of the impregnation, the specificities of the reinforcement itself, the pressure and thermal energy applied during the deposition process, the environmental conditions, the aging of the material before and after the deposition process, and others.

On the other hand, when dry fiber reinforcements are used in the manufacturing of composite laminate, the tack or adherence of the material is mainly linked to the characteristic of a binder (thermoset or thermoplastic) and/or veil (thermoplastic) applied on the surface of the reinforcement. This tack or adherence is also linked to the pressure and thermal energy applied during the deposition process, the specificities of the reinforcement, environmental conditions, etc.

In both cases above, the tack or adherence is critical in the application of the first layer of the laminate over the laying tool, and the material of the laying tool, the characteristics of its surface (surface roughness, surface preparation, presence of additives), and its temperature are key factors for the proper adherence of the reinforcement. Furthermore, it is also critical the tack or adherence in the application of the rest of layers of the laminate over other layers, and the material of these other layers, the characteristics of their surface and their temperature are also taken into account for the adherence between layers in the laminate.

There are known standard procedures and devices to quantitatively measure or qualitatively estimate the tack of different materials, specifically for the case of adhesive films and prepregs. For example, there exists a rolling ball tack test called Standard Test Method for Tack of Pressure-Sensitive Adhesive by Rolling Ball wherein the tack is related to the distance a ball travels along an adhesive surface. In addition, there exists a loop tack test called Adhesives-Tack measurement for pressure sensitive adhesives—Determination of loop tack, wherein the tack is related to the energy required to debond the loop from a surface.

However, these known procedures and devices have the following drawbacks for its use in an industrial environment:

They are oriented to be used in a laboratory environment.
They require the use of complex apparatus, procedures and qualified personnel.
The test results are highly dependent on the test conditions and the personnel involved.
The tests require the extraction of witness specimens. Representativeness is thus linked to the amount of specimens per batch, and how they are selected. A proper balance between effort and benefit should be considered to minimize impacts in production time and cost.
Due to their complexity, the tests are generally only performed at the material supplier site, or when the material is received at the customer site, but almost never in production. Thus, the aging of the material during its storage at low temperature, the aging during its tempering and room temperature storage, the aging during the manufacturing operations, the changes in the environmental conditions during manufacturing (e.g., relative humidity has a large variation along the 24 h of the day even in a clean room) are not considered.

Therefore, the tack data obtained are not sufficiently representative of the real conditions of the material used in production.

Moreover, the availability of reliable process data, including tack data, is relevant to allow maintaining the machine in an optimum process window, avoiding the continuous intervention of the operator to maintain the machine in acceptable conditions based on subjective judgement, strongly dependent on the operator and its experience.

Specifically, the availability of tack or adherence data would be a clear enabler for the implementation or advanced manufacturing systems both for prepreg and dry fiber reinforcements that, linked with machine learning methods, would allow that manufacturing concepts require support high rate production environments.

The present invention provides a new method for automatically determining the tack or adherence in a composite material in real conditions by means of a laying machine which is the same one that manufactures the composite laminate.

SUMMARY OF THE INVENTION

The present invention provides a solution to the aforementioned problems.

The invention proposes a method for determining a debonding energy between layers of a laminate and a laying machine.

In a first inventive aspect, the invention provides a method for determining a debonding energy between a first layer and a second layer of a laminate of composite material by means of a laying machine comprising at least one end effector, the method comprising the following steps:

debonding at least part of the second layer from the first layer by at least a movement of a component of the end effector of the laying machine that causes the second layer to be pulled relative to the first layer, measuring at least a pulling force applied on the second layer and at least the pulling movement of a component of the end effector during step a), and determining the debonding energy between the first and second layer based at least on the measured pulling force and the measured pulling movement.

The present invention provides a method for determining a debonding energy in a composite material laminate by means of a laying machine. This debonding energy that is determined represents the tack or adherence of the materials that conform the composite material laminate. Particularly, the present method determines the debonding energy between at least two layers, specifically a first and a second layer. Throughout this document, it will be understood that the laminate and specifically these first layer and second layer may be made of or may comprise a fiber reinforced composite material, more particularly with preimpregnated reinforcements or dry fiber reinforcements.

The first layer and the second layer of composite material conform a composite material laminate so that when these first and second layers are laminated by a laying machine, a bonding is provided between these first layer and second layer. The laminate may comprise more than two layers.

For determining the debonding energy between two layers of composite material, measurements are performed laying composite material by an end effector of a laying machine and performing a routine of debonding. The end effector is the component of the laying machine in charge of carrying out the lamination or deposition of material either in the form of a tape or tow. That is, the composite material can be deposited as tapes by means of an automated tape laying (ATL) machine, or as tows by means of an automated fiber placement (AFP) machine. Throughout this document, a layer of a composite laminate will be understood as a material ply that comprises a tape or tow of fiber reinforced composite material or a plurality of tapes or tows of fiber reinforced composite material.

Specifically, forces are applied to the composite material under test and movements of components of the end effector are measured to determine the debonding energy between layers of the composite material. With the data obtained from the measurements, the debonding energy of the composite material laminate in the tested conditions is determined to know the tack or adherence of this particular composite material in the laminate.

The present method comprises a step a) of debonding at least part of the second layer from the first layer by pulling the second layer relative to the first layer. To pull the second layer from the first layer, at least a movement of the end effector of the laying machine or of at least one component of the end effector is performed. That is, by moving at least a component of the end effector, the second layer is pulled relative to the first layer so that at least part of the second layer is debonded from the first layer.

The movement of the end effector or of a component of the end effector may be a translation along one or more directions, a rotation around one or more axes or any combination of translation(s) and rotation(s). One or several components of the end effector, or the whole end effector, may be moved to pull the second layer. The resulting pull on the second layer has at least a non-null component along a direction orthogonal to the plane of the laminate—or to a local tangent of the laminate.

The step a) of debonding is performed once both the first and second layers are already at least partially laminated. Specifically, previously to step a), the first layer is laminated over a laying tool or a test plate or another composite material layer, and then the second layer is laminated over the first layer.

In a method according to the invention, while the step of debonding is carried out, a pulling force and a pulling movement are measured. Particularly, the method comprises a step b) of measuring a pulling force applied on the second layer and a corresponding pulling movement of at least one component of the end effector of the laying machine that is moved in step a). These pulling forces and pulling movements cause at least part of the second layer to be debonded from the first layer. This step b) of measuring can be carried out simultaneously with step a) of debonding.

In embodiments wherein the movement of a component of the end effector is a translation of the component, either in isolation or as a result of the translation of the whole end effector, the pulling movement measured at step b) is a displacement of the component. In embodiments wherein the movement of a component of the end effector is a rotation of the component, the pulling movement measured at step b) is a rotation of the component. In embodiments wherein the movement of a component of the end effector comprise a translation and/or a rotation of one or more components, step b) may comprise measuring a displacement and/or a rotation of the one or more components.

Furthermore, the method comprises a step of determining the debonding energy between the first layer and the second layer. The debonding energy is calculated by integrating the pulling force applied to the second layer along a relative displacement during debonding. In the particular embodiment, wherein the movement applied in step a) is a displacement of a component of the end effector, the relative displacement between the component of the end effector and the first layer is taken into account for calculating the debonding energy. In the particular embodiment, wherein the movement applied in step a) is a rotation, this rotation provides a displacement of a length of composite material, and it is this displacement that is taken into account in calculating the debonding energy as mentioned before. In particular, the debonding energy is determined based at least on the pulling force and the pulling movement measured during debonding at least part of the second layer from the first layer of the laminate. Furthermore, the debonding energy may be normalized by dividing this debonding energy by the surface of the material debonded or by the length of material debonded for a predetermined width of the material tape/tow.

The present invention allows the use of an end effector of a laying machine to automatically determine the debonding energy of a composite material laminate without modifying the laying machine, but only programming a routine that would be executed by a numerical control of such laying machine. That is, no mechanical modification of the laying machine is necessary, such that an existing laying machine may be used to perform a method according to the invention.

Modifying a programming of a control unit of the laying machine allows to obtain a machine according to the invention. This operation may be automatically performed by a laying machine or on demand as part of standard manufacturing procedures.

Therefore, advantageously, the present method allows assessing the tack or adherence between layers of composite material by means of the same laying machine that carries out the lamination of these layers of composite material. At the same time that two composite material layers are being laminated, their debonding energy (as representative of the tack or adherence) can be determined, and this tack result is very reliable since the actual laying-out conditions are taken into account.

Compared with the prior art, the present invention proposes a solution in which the debonding energy can be determined by means of the laying machine itself without the need to carry out tests by means of other tooling.

Moreover, the present invention advantageously allows performing the method for determining the debonding energy of a material in a manufacturing environment without the need to be performed in a laboratory.

Since the present method is performed by already known laying machines, although with some adjustments as the invention proposed, it is not necessary to use complex apparatus or qualified personnel to determine the debonding energy of a material.

Therefore, the present invention provides a method that advantageously determines debonding energy that is representative of the tack data on the real conditions of the material used in manufacturing.

In a particular embodiment, the method further comprises before step a):
  laying a first layer of composite material by the end effector of the laying machine, and
  laying a second layer of composite material on the first layer by the end effector of the laying machine.

Firstly, a first layer of composite material is laminated by the end effector on a surface (corresponding to a surface of a laying tool or a test plate or another composite material layer), and then a second layer of composite material is also laminated by the end effector on the first layer. The end effector of the laying machine is configured to cut the first layer once it is completely deposited, and then starts depositing or laminating the second layer over the first layer.

In a particular embodiment, before step a) the end effector of the laying machine stops laminating the second layer on the first layer and, without cutting the second layer, the end effector releases a predefined length of additional composite material as a continuation of the second layer composite material already laminated, and the end effector is displaced to a predetermined position.

According to this embodiment, once at least part of the second layer is laminated on the first layer, the end effector of the laying machine stops laminating the second layer and without cutting this second layer the end effector releases a predefined length of additional composite material in the form of tape or tow, as appropriate. This length of additional composite material released corresponds to a continuation of the second layer that is not laminated. After this, the end effector of the laying machine is displaced to a predetermined position. As a result of the displacement of the end effector to a predetermined position the released composite material may be in tension or stretched between the laminated portion of the second layer and the position to which the end effector moved. However, in the event that this is not the case, the method comprises applying tension to the released predefined length of composite material by a routine of movement of the end effector. This routine of movement is preferably a translation or displacement, in particular a translation with a non-zero component orthogonal to the plane of the laminate. Tension is applied to this released predefined length of composite material so that the second layer can be debonded at least partially from the first layer at least by means of at least moving (i.e., displacing and/or rotating) a component of the end effector and pulling the second layer relative to the first layer.

Once the released composite material is stretched or in tension, then the end effector of the layer machine or at least one component thereof starts moving relative to the first layer. For example, the end effector can be moved upwards or backwards, one or several components of the end effector can be displaced or rotated, or a combination of the above. This movement causes the second layer to be debonded from the first layer. The pulling force applied on the second layer and the pulling movement performed by the end effector or by at least one component thereof are measured to determine the debonding energy between the first and second layers.

In a particular embodiment, step a) comprises displacing the end effector relative to the first layer so that a dancer element of the end effector is consequently displaced, and the second layer is at least partially debonded from the first layer, and step b) comprises measuring the displacement of the dancer element relative to the first layer and the pulling force provided by the dancer element as result of its displacement.

The known laying machines comprise a dancer element that is configured to maintain a steady laying tension in the end effector and allows to compensate transient effects. The movement of the dancer element can be managed by a spring element. In a more particular embodiment, the displacement of the dancer element is measured by a linear variable differential transformer (LVDT) sensor located in the end effector of the laying machine. Due to a movement of the end effector upwards or backwards or a combination of both, the dancer element of the end effector is displaced and consequently the second layer is at least partially debonded from the first layer. In this particular case, the pulling movement of a component of the end effector, which is measured in step b), corresponds to the displacement of the dancer element relative to the first layer, and the pulling force applied to the second layer which is also measured in step b) corresponds to a pulling force provided by this dancer element as result of its movement.

In a more particular embodiment, step b) comprises measuring a torque in a material spool of the end effector as a result of the end effector movement.

The end effector of the laying machine further comprises a material spool, e.g., tape or tow spool, configured to stock the composite material to be laminated. In this sense, the laying machine lays the composite material stored in this material spool by means of the movement of the end effector. Specifically, the composite material is wound in the material spool, so that, for laminating this composite material is unwound from the material spool to be deposited as a layer.

In this embodiment the torque applied by the material spool is also measured as result of the end effector movement for determining the debonding energy between composite material layers as representative of the tack or adherence of this composite material. That is, in step b) the pulling force applied to the second layer corresponds to the pulling force provide by the dancer element as result of its movement and the torque applied by the material spool. In this case, both pulling force provided by the dancer element and the torque in the material spool are measured in step b) of the present method. In a more particular embodiment, the torque in the brake of the material spool can be also measured by the present method.

In a particular embodiment, step a) comprises rewinding, on a component of the end effector of the laying machine, already unwound composite material that is a continuation of the second layer composite material already laminated so that the second layer is at least partially debonded from the first layer, and step b) comprises measuring the rotation of the component and the torque applied on the same component.

As an alternative to the displacement of the end effector or in combination with this displacement of the end effector, in this embodiment the method also comprises rewinding already unwound material. Particularly, the already unwound composite material is a continuation of the second layer composite material given that the composite material of this second layer is not cut once a portion of this second layer is already laminated. Thus, a portion of the composite material of the second layer is laminated, other portion is unwound through the end effector and the rest is wound on a component of the end effector. This operation of rewinding already unwound composite material causes the second layer to be at least partially debonded from the first layer. When this occurs, the method measures the rotation of the component to which the material is rewound, and the torque applied to the same component in order to determine the debonding energy. In this case, the pulling force applied to the second layer, which is measured in step b), corresponds to the torque applied by the component of the end effector divided by the distance between the center of the component and the point of application of the torque in such component. In addition, to determine the debonding energy, the torque divided by the distance between the center of the component and the point of the application of the torque in the component is multiplied by the length of material rewound by such component of the end effector.

Further, the pulling movement, also measured in step b), corresponds to the rotation of the component of the end effector. From this measured rotation a displacement of a length of composite material is determined. In addition, the method can also consider the length of composite material that is already wound in the component prior to the rewinding for determining a more precise length. This material length is then used for calculating the debonding energy in step c).

This component on which composite material can be rewound can be a material spool (disclosed above) or an adding system. The adding system is also comprised in the end effector of the laying machine and is configured to feed composite material in the end effector to prepare the laying of the following course. This adding system is also configured to rewind material on demand or as a dynamometer. In the case where the adding system is used as a dynamometer, this adding system is configured to measure the tension applied to the composite material by measuring the resultant torque in this adding system.

In a more particular embodiment, the component of the end effector on which composite material is rewound is a material spool and rewinding of composite material by this material spool causes the displacement of a dancer element of the end effector and the debonding of at least part of the second layer from the first layer, and step b) also comprises measuring the displacement of the dancer element. That is, when composite material is rewound by a material spool, the dancer element can be consequently displaced, and the second layer is debonded from the first layer. In this particular embodiment, the pulling force applied to the second layer corresponds to the torque applied by the spool material, and the pulling movement of a component of the end effector corresponds to the rotation of the spool material and the displacement of the dancer element, the force, rotation and displacement being measured in the step b) of the present method to determine the debonding energy.

In a particular embodiment, the laminate is laminated on a test plate comprising force measuring means, and step b) comprises measuring, by the force measuring means, the pulling force applied on the laminate while the second layer is at least partially debonded from the first layer. Since the composite material is laminated on a test plate with force measuring means, when the second layer is at least partially debonded from the first layer, the force applied to the second layer is measured over time by the force measuring means. In this embodiment, the pulling force applied to the second layer to be debonded from the first layer corresponds to the force measured by the force measuring means comprised in the test plate. In a more particular embodiment, the force measuring means is a dynamometer.

According to the above particular embodiment, the present method further comprises locking an adding system to apply tension to the composite material and displacing of the end effector relative to the first layer so that the second layer is at least partially debonded from the first layer. In this embodiment, the pulling movement of a component of the end effector corresponds to the displacement of the end effector itself, and this displacement is also measured in step b).

In a particular embodiment, the second layer forms a pulling angle with respect to the first layer during debonding in step a), wherein the pulling angle is different from 0.

As already described above, a part of the material is laminated as second layer over the first layer and other part of material is released from the end effector and corresponds to unwound material. This unwound material or released material is a continuation of the second layer (without being laminated) that forms a pulling angle with respect to the first layer. This pulling angle corresponds to the angle with which the second layer is pulled or displaced relative to the first layer to be debonded from this first layer. The pulling angle is different from 0 to ensure that it is possible to detach the second layer from the first layer, that is, to have at least one non-null orthogonal component (relative to the laminate surface) of the pulling force at the separation point between the second layer and the first layer.

In a particular embodiment, the method further comprises measuring at least one environment condition and/or at least one process condition.

The environment condition may be temperature and/or relative humidity in the room where the present method is performed. Some of the process conditions are energy applied with the laying machine heater, laying temperature corresponding to the temperature at a nip point where the composite material is pressed against the surface where it is deposited, time between laying and debonding composite material, and debonding speed.

The environment and/or process conditions are considered together with the determined debonding energy as representative, in a more precise and reliable way, of the tack or adherence of composite materials that conform the composite material laminate.

In a particular embodiment, the debonding energy is determined in step c) by a processing unit of the laying machine and based on the measurements performed in step b). In this embodiment the laying machine further comprises a processing unit configured to process the data measured during the step of debonding, and optionally other parameters as environment and/or process conditions, and to determine based on these measurements the debonding energy (as representative of the tack or adherence of composite material).

In an embodiment the present method further comprises a step of recording the data measured in step b) and the data determined in step c). In this sense, a database can be generated in order to store data obtained testing the tack or adherence of particular composite materials with specific conditions.

Thus, if there is a database of tack or adherence data that has been obtained testing the same composite material with different levels of aging in the same environmental and process conditions, it is possible to correlate the results of the test with the database to determine the real conditions of the composite material.

Furthermore, if there is a database of tack data that has been obtained testing the same composite material with different levels of aging in different environmental and process conditions, and those data together with environmental and/or process conditions, laying machine parameters and/or quality data of the composite material structure to be manufactured that have been also recorded, it is possible to correlate them to determine the optimum process adapted to the conditions of the composite material.

In a second inventive aspect, the invention provides a laying machine configured to perform the method according to the first inventive aspect, the laying machine comprising:
an end effector configured to laminate composite material, the end effector comprising:
a material spool configured to unwind and rewind the composite material, or
a dancer element, the dancer element being movable to keep a steady tension of the composite material, or
any combination of the above;
a processing unit configured to determine the debonding energy according to step c) of the method,
a motion sensor configured to measure at least the pulling movement of a component of the end effector during debonding, and
a force sensor configured to measure at least the pulling force applied to second layer during debonding.

The present laying machine is configured to perform a method for determining the debonding energy between composite material layers of a laminate. This laying machine comprises a motion sensor and a force sensor for allowing measuring both the pulling movement of a component of the end effector and the pulling force applied to the second layer for debonding this second layer from the first layer. Based on these measurements that the laying machine is configured to take, the laying machine is also configured to determine the debonding energy of composite material by a processing unit. The pulling movement may be performed by one or several components of the end effector such as a dancer element and/or a material spool, by the displacement of the whole the end effector, or by the displacement and/or the rotation of any of the components of the end effector in combination with the displacement of the end effector itself In a particular embodiment, the laying machine further comprises an adding system for unwind and rewind composite material.

In a particular embodiment, the laying machine comprises a torque sensor configured to measure the torque applied by a component of the end effector. More specifically, the torque is measure on a material spool or on an adding system.

In a particular embodiment, the laying machine comprises a test plate configured to lay out a laminate on it, the test plate comprising force measuring means configured to measure the pulling force applied on the laminate while the second layer is at least partially debonded from the first layer.

All the features described in this specification (including the claims, description and drawings) and/or all the steps of the described method can be combined in any combination, with the exception of combinations of such mutually exclusive features and/or steps.

BRIEF DESCRIPTION OF THE DRAWINGS

These and other characteristics and advantages of the invention will become clearly understood in view of the detailed description of the invention which becomes apparent from a preferred embodiment of the invention, given just as an example and not being limited thereto, with reference to the drawings.

DETAILED DESCRIPTION OF THE PREFERRED EMBODIMENTS

The present invention provides a method for determining the debonding energy between a first layer (1) and a second layer (2) of a laminate (9) of composite material by means of a laying machine comprising an end effector (10). Both the first layer (1) and the second layer (2) are formed by a material supplied by the laying machine and that is deposited or laminated by the end effector (10) of this laying machine.

In order to determine the debonding energy, the second layer (2) is at least partially detached from the first layer (1) and for this at least a component of the end effector (10) is displaced so that a displacement is applied to the composite material in such a way that the second layer (2) is pulled to be at least partially detached from the first layer (1).

Figure 1:
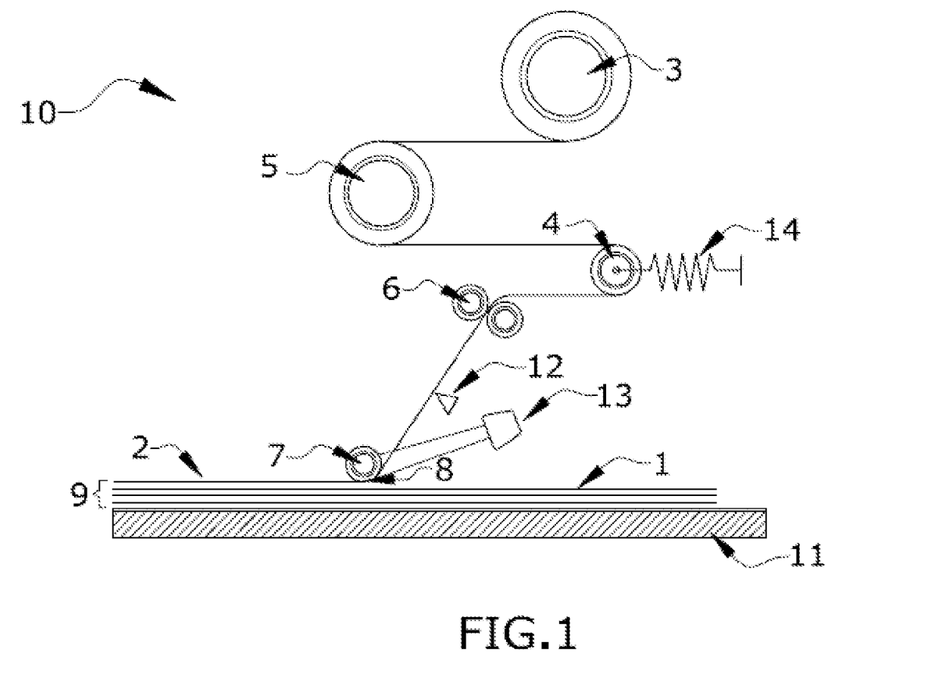
FIG. 1 shows a schematic view of an end effector of a laying machine according to an embodiment of the present invention.
Figure 2:
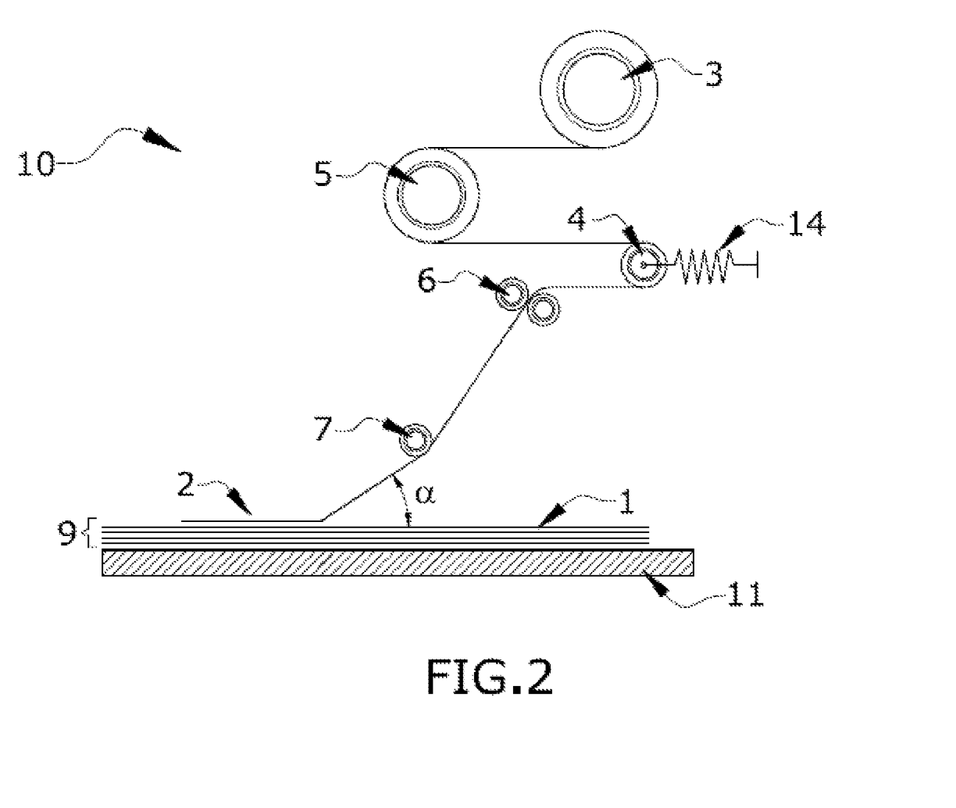
FIG. 2 shows a schematic view of the end effector of a laying machine of FIG. 1 according to an embodiment of the present invention.

FIGS. 1-2 show an end effector (10) of a tape/tow laying machine according to the invention, particularly, FIG. 1 shows the end effector (10) depositing composite material (tape/tow) and FIG. 2 shows the end effector (10) configured to start debonding the second layer (2) from the first layer (1) according to the present method.

According to FIG. 1, the laying machine lays the composite material stored in a material spool (3) (tape/tow spool) by means of the movement of the end effector (10). The deposition of this composite material is carried out on a surface of a laying tool (11) and results in a laminate (9) of composite material.

A pressure roller (7) presses the tape/tow of material at a nip point (8) against the first layer (1) already deposited, allowing the adherence of the composite material between layers (1, 2). At the same time the pressure roller (7) presses the composite material, a heater element (13) provides heat at the nip point (8) for facilitating the deposition of this composite material. The end effector (10) may comprise an energy sensor for measuring the energy applied with the heater element (13) and/or a temperature sensor for measuring the temperature at the nip point (8).

A programmed movement of the end effector (10) parallel to the laying tool (11) together with the pressure applied with the pressure roller (7) lays the composite material which is unwound from the material spool (3). Simultaneously, a protective polyethylene carrier is rewound into a poly reel (5), only for the case wherein the material to be deposited is prepreg and not dry fiber. A break in the material spool (3) controls the excessive unwinding of the composite material. A motor connected to the material spool (3) can be also used to add or rewind composite material as the process requires. The end effector (10) comprises a torque sensor that measure the torque of the break in the material spool (3) or the torque of the motor.

The end effector (10) further comprises a dancer element (4) for maintaining a steady laying tension for the composite material by its movement. The movement of the dancer element (4) is managed by a spring element (14) which allows to compensate transient effects. The end effector (10) comprises a displacement sensor configured to measure the displacement of the dancer element (4). In a particular example, this displacement sensor is a LVDT sensor.

According to the laying process, the already programmed length of the composite material to be deposited is extracted from the material spool (3) and trimmed by a blade of a cutter (12). The end effector (10) continues its displacement parallel to the laying tool (11) up to the end of a programmed position and concludes the deposition of a layer of composite material.

The end effector (10) further comprises an adding system (6) that is disengaged during the laying steps and is activated to feed material in the end effector (10) for preparing the laying of the following course. This adding system (6) can be also used to rewind composite material in demand or as a dynamometer to measure the tension applied to the composite material by measuring the resultant torque in the adding system (6). The torque in the adding system (6) is measured by a torque sensor.

The end effector (10) described above is configured according to the invention to perform a programmed routine of movements for at least partially debonding a layer from another layer of a composite laminate in order to automatically measure at least a pulling movement in the end effector (10) and a pulling force applied to a layer during its debonding. Based on these measurements, the present method determines the debonding energy between layers of a composite material. This debonding operation is performed by actual productions means (laying machine) and can be carried out automatically or on demand as part of the manufacturing procedure.

According to FIG. 2, the end effector (10) shown is the same as the one in FIG. 1 and described above. Specifically, in FIG. 2 the cutter (12) and the heater element (13) are not shown since they do not participate in the debonding operation. Anyway, in an embodiment the present method considers the temperature conditions measured by the temperature sensor in the nip point (8) (shown in FIG. 1) and/or the energy measured by the energy sensor in the heater element (13) (shown in FIG. 1), and the determined debonding energy, as representative of the tack between a first (1) and second (2) layers of a composite material laminate (9). That is, the end effector (10) shown in FIG. 2 only shows the components which can be actuated in the present method for at least partially debonding the second layer (2) from the first layer (1).

The composite material mentioned above referring to FIGS. 1 and 2 is a fiber reinforced composite material that can be in the form of tape or tow or a plurality of tapes or tows. That is, the layers that conform the composite material laminate (9) comprise a simple tape or tow or a plurality of tapes or tows. Through this document, the term "material" or "composite material" has been used interchangeably to refer to a tape or tow of material or a plurality of tapes or tows.

A particular example of a method according to the present invention is described below. This method is able to determine the debonding energy between a first layer (1) and a second layer (2) of a composite material laminate (9) by means of a laying machine that comprises an end effector (10) as shown in FIGS. 1-2.

The method comprises a step of depositing at least the first (1) and second (2) layers as follows:
laying a first layer (1) of composite material by the end effector (10) of the laying machine, and
laying a second layer (2) of composite material on the first layer (1) by the end effector (10) of the laying machine.

The first layer (1) can be deposited on another layer of composite material that also forms part of the laminate (9), or can be deposited on a laying tool (11). Particularly, the deposition of second layer (2) is shown in FIG. 1 once the first layer (1) is already deposited.

When the second layer (2) is at least partially deposited, the end effector (10) stops laminating the second layer (2) on the first layer (1) and, without cutting this second layer (2), the tape spool (3) of the end effector (10) releases a predefined length of additional tape of material. The end effector (10) then moves to a predetermined position so that the released tape of composite material is tensioned between the already laminated second layer (2) and the tape spool (3) as shown in FIG. 2. In a particular example, if the released predefined length of tape is not stressed once the end effector (10) is displaced to a predetermined position, then the method further comprises before step a) applying tension to the released predefined length of tape by displacing the end effector (10) relative to the first layer (1).

Specifically, FIG. 2 shows the end effector (10) displaced from the laminate (9) compared with its position in FIG. 1 where it is performing the deposition of the second layer (2) on the first layer (1). Displacing the end effector (10) to a predefined position, as shown in FIG. 2 allows the roller (7) reach a position where it cannot exert pressure force on the laminate (9).

Once the end effector (10) is positioned to the predefined position, the method performs a step a) debonding at least part of the second layer (2) from the first layer (1) by at least a movement of a component of the end effector (10) of the laying machine that causes the second layer (2) to be pulled relative to the first layer (1). Simultaneously to this step a), the method performs a step b) of measuring at least a pulling force applied on the second layer (2) and at least the pulling movement of a component of the end effector (10) during step a).

According to step a), the method performs a displacement of the end effector (10) relative to the first layer (1) so that a dancer element (4) of the end effector (10) is consequently displaced and the second layer (2) is at least partially debonded from the first layer (1). The displacement of the dancer element (4) relative to the first layer (1) is measured according to step b) of the present method, and the pulling forced provided by the dancer element (4) as result of its displacement is also measured in step b). In this case, the pulling force applied to the second layer (2) corresponds to the pulling force provided by the dancer element (4), and the pulling movement measured in this method corresponds to the displacement of the dancer element (4).

In addition, the method may further measure in step b) the torque and/or the rotation in the tape spool (3) as result of the end effector (10) movement. For this case, the pulling force applied on the second layer (2) corresponds to the torque applied by a tape material (3), and the pulling movement corresponds to the displacement of the end effector (10), displacement of the dancer element (4) and the rotation of the tape material (3).

Additional to the previous step a) disclosed or as an alternative to this, in an embodiment the method performs a rewinding stage. In particular, the already unwound tape that forms part of the second layer (2) as a continuation of the same is rewound on the tape spool (3) or on the adding system (6). By means of this tape rewinding, the second layer (2) is at least partially debonded from the first layer (1). The rotation of the tape spool (3) or adding system (6) and the torque applied by the same are measured in the step b). Particularly, the pulling force applied on the second layer (2) corresponds to the torque applied on the tape spool (3) and/or the adding system (6) divided by the distance between the center of the tape spool (3) and/or the adding system (6) and the nip point of application of the torque in the tape spool (3) and/or adding system (6) respectively. Further, the pulling movement corresponds to the rotation of the tape spool (3) and/or the adding system (6). Moreover, from the measured rotation a displacement of a length of material is determined for then calculating the debonding energy in step c). Moreover, the length of tape that is stored in the tape spool (3) or in the adding system (6) before rewinding unwound tape can be also measured in the present method to be able to determine more precisely the length of material that is rewound. For determining the debonding energy in step c), the torque divided by the distance between the center of tape spool (3) and/or the adding system (6) and the point of the application of the torque in the tape spool (3) and/or the adding system (6) is multiplied by the length of material rewound by tape spool (3) and/or the adding system (6).

Furthermore, in step a) rewinding tape of material by the material spool (3) causes the displacement of a dancer element (4), and therefore, the displacement of the dancer element (4) is further measured in step b). That is, the pulling movement for this embodiment corresponds both to the rotation of the material spool (3) and the displacement of the dancer element (4). From the rotation of the material spool (3) the displacement of a length of material is determined for then calculating, together with the displacement of the dancer element (4), the debonding energy in the step c) of the present method.

In order to pull on the tape of material from the adding system (6) or the tape spool (3), the roller (7) must be in an upwards position (compared FIG. 2 with FIG. 1 where the end effector (10) is performing a deposition of material) in order to let the second layer (2) to be debonded from the first layer (1).

Prior to starting the debonding the second layer (2) from the first layer (1), and once the end effector (10) or any of its components is displaced if needed, the tape of material of the second layer (2) that is not deposited forms a pulling angle (a) relative to the first layer (1). That is, in the moment when the second layer (2) is going to be detached from the first layer (1), this second layer (2) forms a pulling angle (a) with respect to the first layer (1). This pulling angle (a) corresponds to the angle that forms this second layer (2) with respect to the first layer (1) when the second layer (2) is pulled away from the first layer (1). According to a particular example, the pulling angle ($\alpha$) varies while the second layer (2) is debonded from the first layer (1). This pulling angle ($\alpha$) is different from 0, and preferably, $0<\alpha\leq180°$.

In another example not shown in FIGS. 1-2, the laminate (9) is deposited on a test plate instead of a tooling plate. This test plate comprises force measuring means, preferably, a dynamometer, configured to measure the force applied on the laminate (9) when the second layer (2) is at least partially debonded from the first layer (1). The test plate can be adapted to increase the adherence between the laminate (9) and the test plate. The force measured by the dynamometer corresponds to the pulling force applied to the second layer (2).

Any of the above forces (torque, rotation, . . . ) measured in step b) or a combination of them provides the pulling forces applied to the second layer (2) during step a). For example, the displacement of the dancer element (4) by means of the actuation of the spring element (14) provides the pulling force. Furthermore, any of the above displacements also measured in step b) or combination of them provides the pulling displacement of the second layer (2).

In addition to the above possible data to be measured, in an embodiment the present method further comprises measuring in step b) environmental conditions such as temperature and relative humidity in the manufacturing room, and/or process conditions such as energy applied with the laying machine heater, laying temperature (temperature at a nip point (8)), time between laying and debonding tape of material, and debonding speed.

All these data obtained in step b) are used in a following step c) of the present method for determining the debonding energy between the first (1) and second (2) layer of a composite material laminate (9). Particularly, the tape placement machine further comprises a processing unit configured to determine the debonding energy based on the data measured in step b) in relation to the pulling movement and the pulling force.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for determining a debonding energy between a first layer and a second layer of a laminate of composite material by means of a laying machine comprising at least one end effector, the method comprising the following steps:
   a) debonding at least part of the second layer from the first layer by at least a pulling movement of a component of the end effector of the laying machine that causes the second layer to be pulled relative to the first layer,
   b) measuring at least a pulling force applied on the second layer and at least the pulling movement of the component of the end effector during step a), and c) determining a debonding energy between the first and second layer based at least on the measured pulling force and the measured pulling movement, wherein step a) comprises displacing the end effector relative to the first layer so that a dancer element of the end effector is consequently displaced and the second layer is at least partially debonded from the first layer, and wherein step b) comprises measuring the displacement of the dancer element relative to the first layer and the pulling force provided by the dancer element as result of the displacement.

2. The method according to claim 1, wherein before step b) the end effector of the laying machine stops laminating the second layer on the first layer and, without cutting the second layer, the end effector releases a predefined length of additional composite material as a continuation of the second layer composite material already laminated, and the end effector is displaced to a predetermined position.

3. The method according to claim 2, further comprising applying tension to the released predefined length of composite material.

4. The method according to claim 1, wherein step b) further comprises measuring a torque in a material spool of the end effector as a result of the end effector displacement.

5. The method according to claim 1, wherein the laminate is laminated on a test plate comprising force measuring means, and wherein step c) comprises measuring, by the force measuring means, the pulling force applied on the laminate while the second layer is at least partially debonded from the first layer.

6. The method according to claim 1, further comprising before step b):
laying the first layer of composite material by the end effector of the laying machine, and
laying the second layer of composite material on the first layer by the end effector of the laying machine.

7. The method according to claim 1,
wherein the second layer forms a pulling angle with respect to the first layer during debonding in step b), and
wherein the pulling angle is different from 0.

8. The method according to claim 1, further comprising measuring at least one of an environmental condition or a process condition.

9. The method according to claim 1, wherein the debonding energy is determined in step c) by a processing unit of the laying machine and based on the measurements performed in step b).

10. A method for determining a debonding energy between a first layer and a second layer of a laminate of composite material by means of a laying machine comprising at least one end effector, the method comprising the following steps:
a) debonding at least part of the second layer from the first layer by at least a pulling movement of a component of the end effector of the laying machine that causes the second layer to be pulled relative to the first layer,
b) measuring at least a pulling force applied on the second layer and at least the pulling movement of the component of the end effector during step a), and
c) determining a debonding energy between the first and second layer based at least on the measured pulling force and the measured pulling movement, wherein step a) comprises rewinding, on a component of the end effector of the laying machine, already unwound composite material as a continuation of the second layer composite material already laminated so that the second layer is at least partially debonded from the first layer, and wherein step b) comprises measuring a rotation of the component and a torque applied on the same component.

11. The method according to claim 10, wherein the component of the end effector is a material spool and the rewinding of composite material by this material spool causes a displacement of a dancer element of the end effector and the debonding of at least part of the second layer from the first layer, and wherein step b) also comprises measuring the displacement of the dancer element.

* * * * *